United States Patent [19]
Raun

[11] 3,937,836
[45] Feb. 10, 1976

[54] ANTIBIOTIC COMPOUNDS FOR RUMINANT FEED UTILIZATION IMPROVEMENT

[75] Inventor: Arthur P. Raun, New Palestine, Ind.

[73] Assignee: Eli Lilly and Company, Indianapolis, Ind.

[22] Filed: June 3, 1974

[21] Appl. No.: 475,720

Related U.S. Application Data

[60] Division of Ser. No. 323,599, Jan. 15, 1973, Pat. No. 3,839,557, which is a continuation-in-part of Ser. No. 220,304, Jan. 24, 1972, Pat. No. 3,794,732.

[52] U.S. Cl................................ 424/283; 424/115
[51] Int. Cl.[2]....................................... A61K 31/35
[58] Field of Search.................... 424/283, 122, 115

[56] References Cited
UNITED STATES PATENTS

| | | | |
|---|---|---|---|
| 3,555,150 | 1/1971 | Gorman et al. | 424/122 |
| 3,577,531 | 5/1971 | Gorman et al. | 424/122 |
| 3,744,732 | 2/1974 | Raun | 424/283 |
| 3,839,557 | 10/1974 | Raun | 424/115 |

OTHER PUBLICATIONS

J. Am. Chem. Soc. (1951) 73:5295–5298.
Stedman's Medical Dictionary (1961) p. 331.
O'Conner et al., J. Anim. Sci., 30, 812–818 (1970).
Purser et al., J. Anim. Sci, 24, 1039–1044 (1965).

Primary Examiner—Leonard Schenkman
Attorney, Agent, or Firm—Joseph A. Jones; Everet F. Smith

[57] ABSTRACT

Antibiotics of the group A204, X537A, dianemycin, monensin, nigericin, and X206, the deshydroxymethyl derivatives of monesin and nigericin, and their physiologically acceptable salts and esters, improve the digestive efficiency of certain herbivorous animals. Oral administration of the antibiotics to ruminant animals having a developed rumen function, and to animals which ferment fibrous vegetable matter in the cecum, changes the digestive fermentation to produce more propionates relative to the production of acetates, thereby improving feed utilization.

10 Claims, No Drawings

ANTIBIOTIC COMPOUNDS FOR RUMINANT FEED UTILIZATION IMPROVEMENT

CROSS-REFERENCE

This application is a division of application Ser. No. 323,599 filed Jan. 15, 1973, now U.S. Pat. No. 3,839,557, which is a continuation-in-part of my copending application Ser. No. 220,304, filed Jan. 24, 1972, now U.S. Pat. No. 3,794,732.

BACKGROUND OF THE INVENTION

For many years, the animal science industry has tried to increase the efficiency of feed utilization by animals. The ruminant animals are of particular economic importance, and so, necessarily, is the efficiency of the utilization of ruminants' feed.

In the course of investigating the efficiency of feed use, the mechanism by which ruminants digest and degrade the components of their feed to form molecules which can be metabolically utilized has been intensively studied. The mechanism of carbohydrate utilization is now well known. Microorganisms in the rumen of the animal ferment the carbohydrate to produce monosaccharides, and then degrade the monosaccharides to pyruvate compounds.

It is to be understood that the rumen produces 2-carbon, 3-carbon, and 4-carbon compounds in the form of acids and salts and other derivatives of the acids. Since it is impossible to identify precisely what form the various compounds take, those compounds are referred to in the art respectively as acetates, propionates, and butyrates.

Pyruvate is then metabolized by microbiological processes to either acetates or propionates. Two acetate compounds may be combined thereafter, still in the rumen, to form a butyrate. Leng, "Formation and Production of Volatile Fatty Acids in the Rumen," *Physiology of Digestion and Metabolism in the Ruminant* (Phillipson et al. ed.), Oriel Press, pages 408–10.

The animal can utilize butyrates, propionates, and acetates with differing degrees of efficiency. Utilization of those compounds, which are collectively known as volatile fatty acids (VFA), occurs after absorption from the gut of the animal. Butyrates are utilized most efficiently, and acetates the least efficiently. However, the relative efficiency of use of butyrates is negated by the inefficiency of the manufacture of butyrates, which must be made from acetates in the rumen.

One of the major inefficiencies in the rumen is in the manufacture of acetates. Since they are made by the degradation of pyruvates, each molecule of an acetate which is produced is accompanied by a molecule of methane. Most of the methane produced is lost through eructation. Since a butyrate is made from two acetate molecules, each molecule of the relatively efficiently used butyrates results in the loss to the animal of two molecules of methane, with all of the associated energy.

Thus, the efficiency of carbohydrate utilization can be increased by treatments which cause the animal to produce propionates rather than acetates from the carbohydrates. Further, the efficiency of feed use can be effectively monitored by observing the production and concentration of propionate compounds in the rumen. If the animal is making more propionates, it will be found to be using its feed more efficiently.

The relative efficiency of utilization of the VFA's is discussed by McCullough, *Feedstuffs*, June 19, 1971, page 19; Eskeland et al., *J. Anim. Sci.* 33, 282 (1971); and Church et al., *Digestive Physiology and Nutrition of Ruminants*, vol. 2 (1971), pages 622 and 625.

It has been well established that the efficiency of feed utilization by a ruminant animal can be readily determined by chemical analysis of the fermentation occurring in the rumen. For example, Marco et al., U.S. Pat. 3,293,038 taught the use of alkylated phenols as feed additives for improved feed efficiency. They illustrated an in vitro rumen fermentation test, and in vivo animal feeding studies, which were evaluated by chemical analysis of the rumen contents for acetates and propionates.

O'Connor et al., *J. Anim. Sci.* 30, 812–18 (1970), reported the results of in vitro rumen fermentation tests on a large number of compounds. German Patent 2,059,407 reported the use of a hemiacetal of chloral and starch as a feed additive which inhibits the formation of methane and produces higher than normal levels of propionic and butyric acids.

Marco et al., U.S. Pat. 3,522,353 taught the use of halogenated acyclic carboxylic acids as feed additives. It was there shown that the compounds produced in vitro increases in propionate production, and also increased feed efficiency in animals fed those compounds. To a similar effect is Erwin et al., U.S. Pat. 3,564,098.

The condition called ketosis is a manifestation of faulty VFA balance, which amounts to a clinical illness. Ruminant animals maintained on a diet which naturally degrades to a high proportion of acetates and low proportion of propionates are likely to suffer from ketosis. Dairy animals are particularly prone to the condition. Under stress, such as the onset of high lactation, insufficient propionates are available. As a result, more acetates are used leading to a high concentration of ketones in the body and especially in the bloodstream. A treatment for ketosis is to feed propionic acid, a precursor of propionic acid, or glucose which tends to metabolize to propionates. Clearly, if the rumen could be caused to produce more propionates than normal from the diet, ketosis incidence could be reduced.

SUMMARY

I have now discovered a novel method of increasing the efficiency of feed utilization by ruminant animals having a developed rumen function. An antibiotic chosen from the group A204, dianemycin, monensin, X537A, nigericin, and X206, the deshydroxymethyl derivatives of monensin and nigericin, and their physiologically-acceptable salts and esters is orally administered to the ruminant animals whose feed efficiency is to be increased.

DESCRIPTION OF THE PREFERRED EMBODIMENT

I have invented a method of improving feed utilization by ruminants having a developed rumen function which comprises oral administration to the ruminants of an effective propionate-increasing amount of a compound chosen from the group A204, dianemycin, X537A, monensin, nigericin, and X206, the deshydroxymethyl derivatives of monoensin and nigericin, and their physiologically-acceptable esters and salts. The preferred antibiotics of my method are monensin and A204.

My invention is useful to ruminants which have a developed rumen function. Young ruminants, basically those still unweaned, function as monogastric animals. They use their simple liquid feeds just as monogastric animals do. As the young ruminants begin to eat solid feed, containing cellulose, starch, and other carbohydrates, the function of the rumen begins to develop, and the microbiological population of the rumen increases. After the animal has eaten solid feed for a time, its rumen reaches its full development and continues to operate throughout the animal's life.

It is to be understood that the usefulness of my method is not limited to animals which are being fattened or to young growing animals. When my method is applied to adult animals, such as dairy cows or breeding stock, its benefit is seen as reducing feed consumption necessary to maintain animal performance.

My invention is functional in all of the ruminants, that is, the animals which have multiple stomachs, one of which is a rumen. The economically-important ruminant animals are cattle, sheep, and goats.

At least a propionate-increasing amount of one of my antibiotics must be administered in order to gain the benefit of the present invention. In general, propionate-increasing amounts are in the range of from about 0.05 mg. of antibiotic per kg. of body weight per day to about 2.5 mg./kg./day. The preferred range of administration rates is from about 0.1 mg./kg./day to about 1.5 mg./kg./day. Those skilled in the art will recognize that the optimum rate of administration for a given animal is variable, and may at times fall outside the ranges here stated.

The compounds which I here disclose as effective in improving feed utilization are all antibiotics of related structures. Each of the antibiotic compounds is made up of a chain of oxygen-containing rings, with a single carboxylic acid moiety at one end of the molecule and one or more hydroxyl moieties at the other end of the molecule.

An unusual complex salt is formed with monovalent metal ions by all of the antibiotics active in my method. A complex is formed between one molecule of the antibiotic and one ion of the metal. The oxygen atoms in the linked rings of the antibiotic molecule complex with the metal ion. Thus, the antibiotic molecule forms a loop or ball around the ion. A weak covalent bond is formed between the ion and each oxygen atom. The ends of the molecule are fastened together by hydrogen bonding between the carboxyl group and a hydroxyl group at the opposite end of the antibiotic molecule. Thus, the ion is completely enclosed within the antibiotic molecule. The unusual result is that the metal salt of the antibiotic is insoluble in water but is soluble in organic solvents.

The ion-transport properties of the antibiotic are significantly affected by its ability to form these unusual complexes. Pinkerton et al., *J. Mol. Biol.* 49, 533–46 (1970).

It is expected that other antibiotics which have the general structure and property just described will be useful in my method. Such compounds clearly fall within the scope of my invention.

Dianemycin has very recently been structurally characterized.

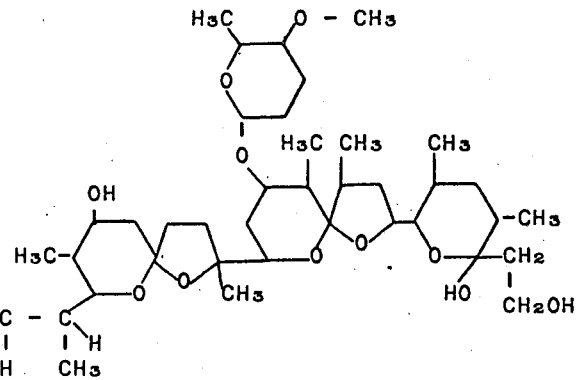
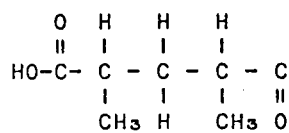

Steinrauf et al., *Biochemical and Biophysical Research Communications* 45, 1279–87 (1971).

Gorman et al., U.S. Pat. 3,577,531 taught the description, preparation, and characteristics of dianemycin, and referred to an earlier article about it by Lardy et al., *Arch. Biochem. Biophysics* 78, 587–97 (1958).

Dianemycin is a fermentation product of an organism which is a strain of *Streptomyces hygroscopicus*, and is on unrestricted deposit under the identifying number NRRL 3444 at the Northern Utilization Research and Development Div., Agricultural Research Service, United States Department of Agriculture, 1815 North University Street, Peoria, Ill. 61604.

Nigericin has been known at various times as helexin C, antibiotic X464, antibiotic K178, polyetherin A, and azalomycin M. It has been structurally characterized by Stainrauf et al., *Biochemical and Biophysical Research Communications* 33, 29 (1968). The structure is shown below.

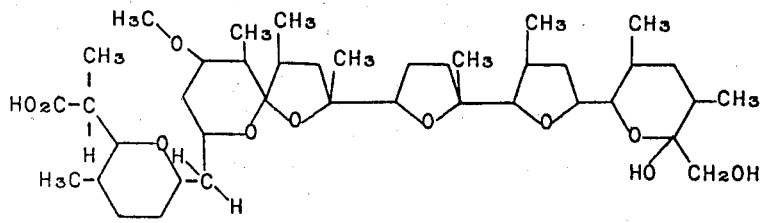

Nigericin was originally reported by Harnes, et al., *Antibiotics and Chemotherapy 1*, 594–96 (1951). It has also been described in Gorman et al., U.S. Pat. 3,555,150.

The organism which produces nigericin, a strain of *Streptomyces violaceoniger*, is on unrestricted deposit as NRRL B1356 at the Northern Research and Development Div., Agricultural Research Service, United States Department of Agriculture.

Nigericin is produced by fermentation in any of several types of fermentation media. It is not produced efficiently in synthetic media, but requires a complex nitrogen source such as fishmeal, distiller's residues, cottonseed meal, or soybean flour. The medium must also include a carbon source such as a starch, a sugar, or the like.

Nigericin is best produced by first inoculating an aerated starter tank with a vegetative inoculum. The contents of the starter tank is used, when the fermentation is proceeding actively, to inoculate a production tank. The production tank is maintained at about 28°C., and is supplied with sterile air at a rate from about half to about twice the tank's volume per minute.

The nigericin is harvested after about 4 to 6 days of growth. Most of the activity is in the cells, which are filtered out of the broth. Extraction with an alcohol, concentration, transfer of the activity first to aqueous alcohol and then to benzene and chromatography isolate the nigericin.

Those skilled in the art will recognize that all the antibiotic production processes discussed below must be conducted under sterile conditions in order to obviate contamination. Specific cautions to that effect will not be given or needed in the examples below.

The starter tank is grown for 3 days at 28°C. One cubic foot per minute of sterile air is bubbled through the medium.

The contents of the starter tank are transferred aseptically to a 550-liter production tank containing the above medium. The fermentation is allowed to continue for 5 days at 28°C., while 20 c.f.m. of sterile air is bubbled through the medium.

The broth is filtered with diatomaceous filter aid. The wet filter cake is extracted with 250 l. of methanol and the extract is concentrated to 45 l. The concentrated extract is extracted with an equal volume of butyl acetate, which is then washed with 0.2M $K_2HPO_4$, washed with water, and concentrated to a paste. The paste is extracted with 4.5 l. of petroleum ether, which is then evaporated to 1 kg. of oil.

The oil is partitioned in 2 l. of two parts of 90% aqueous methanol and three parts of petroleum ether, and then the petroleum ether is extracted twice with more 90% aqueous methanol. All the aqueous methanol portions are combined and concentrated to an oil, which is dissolved in benzene and adsorbed on an 1800 g. activated alumina column. Elution with, in succession, benzene, benzene + 10% ether, ether, and ether + 10% ethanol recovers the nigericin activity as the mixed sodium-potassium salt, m.p. 225°–35°C. Conversion to the free acid, m.p. 170°–72°C., is accomplished by partitioning the salt between ether and dilute hydrochloric acid.

Monensin was described by Haney et al., U.S. Pat. 3,501,568. The substance known as monensin is actually a mixture of four factors, all of which are included in the term monensin. The structure shown below is the acid form of monensin factor A.

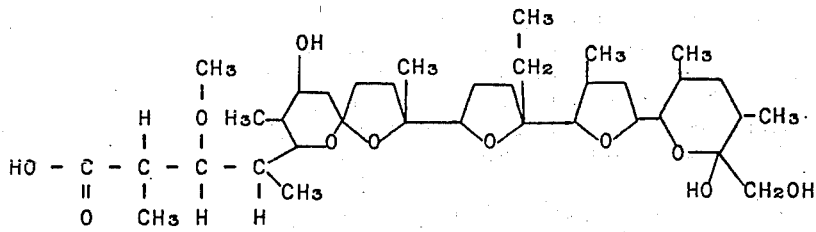

The example below shows in more detail the method of producing nigericin.

EXAMPLE 1

A vegetative inoculum is prepared by growing the Streptomyces organism known as NRRL B1356 on agar slants made up of 10 g. of dextrin, 2 g. of an enzyme-digested casein, 1 g. of beef extract, 1 g. of yeast extract, and sufficient water to make 1 liter. The slants are grown for 3 days at 28°C.

The spores are harvested from the slants and transferred to a 30-liter starter tank containing the following sterile medium.

| | |
|---|---|
| 3% | soybean flour |
| 2% | brown sugar |
| 0.5% | cornsteep liquor |
| 0.1% | $K_2HPO_4$ |
| | tap water |

Monensin is produced by fermentation by an organism which is on unrestricted deposit under the number ATCC 15413 at the American Type Culture Collection, 12301 Parklawn Drive, Rockville, Md. 20852.

Antibiotic A204 is described in U.S. Pat. 3,705,238, issued Dec. 5, 1972. The term A204 is used to include the several factors obtained by fermentation with the A204-generating organism on unrestricted deposit as NRRL 3384 at the Northern Utilization Research and Development Division, Agricultural Research Service, U.S. Department of Agriculture, Peoria, Ill. Details of the fermentation process are given in the above application.

Factor I of A204 is the most important and abundant. Factor II comprises about 5 percent of the A204 mixture produced. The other factors are produced in minor amounts. The structure below is that of the acid form of A204 I.

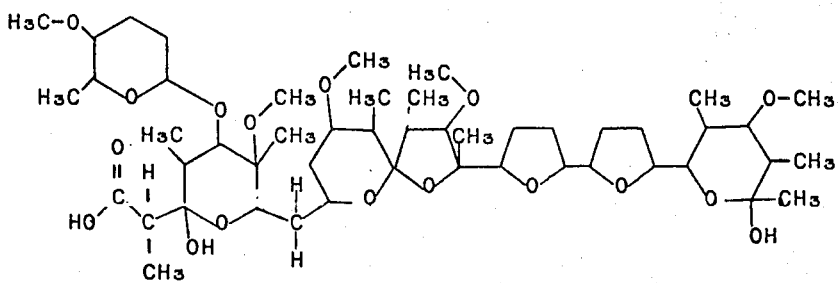

Antibiotic X206 was first reported in 1951, Berger et al., *J. Am. Chem. Soc.* 73, 5295–98 (1951). The Streptomyces organism from which it can be grown is available from the International Center of Information on Antibiotics, c/o L. Delcambe, 32, Bd. de la Constitution, Liege, Belgium, which lists the organism on page 31 of its Bulletin No. 3 (1966).

X206 has been characterized as a molecule very similar to the other antibiotic compounds of my method.

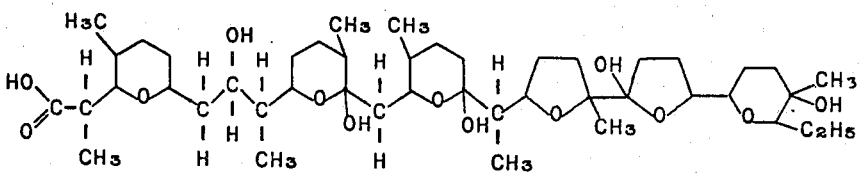

Blount et al., *Chemical Communications*, 1971, 927–28.

The same article illustrates X206 as being wrapped around a monovalent metal ion in the same way that the other antibiotics complex with ions. The compound is aptly described as "wrapped around the silver in such a way that its backbone describes a path similar to that of the seam on a tennis ball."

The general methods of producing X206 are very similar to the methods of producing nigericin which have been described. X206 is harvested from both the fermentation broth and from the cells. After filtration of the broth, it is extracted with an ester solvent. The solvent is concentrated and extracted with an aqueous buffer at alkaline pH. The product is in the solvent phase.

The cells are extracted with alcohol and concentrated. The concentrate is extracted with an ester solvent, which is concentrated. Chromatography of both of the extracts isolates X206.

The following example illustrates the production of X206.

EXAMPLE 2

The Streptomyces organism, obtained from the I.C.I.A. as above, is used to grow a vegetative inoculum. Spores are inoculated on agar slants made as follows.

| | |
|---|---|
| 10 g. | dextrin |
| 2 g. | enzyme-digested casein |
| 1 g. | beef extract |
| 1 g. | yeast extract |
| | water to make 1 liter |

After 3 days at 28°C., spores are harvested from the slants and transferred to a 30-liter starter tank containing the following medium.

| | |
|---|---|
| 3% | soybean flour |
| 2% | brown sugar |
| 0.5% | cornsteep liquor |
| 0.1% | $K_2HPO_4$ |
| | water |

The starter tank is supplied with 1 cubic foot per minute of sterile air which is bubbled through the medium. After 3 days of growth at 28°C., the starter tank is harvested. Its contents are transferred aseptically to a 550 l. production tank containing the above medium. The fermentation is supplied with a continuous flow of 20 c.f.m. of sterile air. Production of X206 reaches its maximum after 6 days of growth at 28°C.

The fermentation broth is filtered with diatomaceous earth filter aid. X206 is present in both the filter cake and the filtrate.

To the filtrate is added 10 percent of NaCl and 50 percent of butyl acetate. After 30 minutes' stirring, the organic layer is separated and concentrated to 5 percent of its volume. The solution is then extracted with ice-cold 0.2M $K_2HPO_4$ with KOH added to pH 8.9. The organic phase is then concentrated to 1 liter.

Xylene is added, and the concentrate is further concentrated to 60 g., which is dissolved in 200 ml. of benzene and adsorbed on a 500 g. activated alumina column. More benzene is added to develop the chromatogram, and the active material is then eluted with ether containing increasing amounts of ethanol up to 23%. The fractions active against Bacillus E are collected.

X206 is harvested from the cells as follows. The filter cake is extracted first with 30 l. of ethanol and then with 200 l. of methanol. The combined alcohol solutions are concentrated to 4 l. and mixed with 10 l. of butyl acetate. The resulting solution is extracted with alkaline ice-cold 0.2M $K_2HPO_4$ solution.

The organic phase is then further concentrated and chromatographically purified in the same manner used for purifying the harvest from the filtrate.

The fractions from the filtrate and from the cake assaying active against Bacillus E are further purified by first dissolving in the smallest possible amount of ether. Then petroleum ether is added and the ether evaporated off. The mixture is cooled to 0°C. for a day and then filtered. The filtrate is concentrated further and the precipitation from petroleum ether is repeated.

The second filtered solution is evaporated and the oily residue dissolved in ether. A large amount of petroleum ether is added and the mixture concentrated with heat until X206 crystallizes. The crystals are the mixed sodium-potassium salt, m.p. 201°–03°C.

The free acid, m.p. 126°–28°C., is prepared by sulfuric acid treatment of the above salt. It is optically active, $[\alpha]_D^{29} + 15°$ in methanol, has no characteristic UV absorption, and is soluble in alcohols, esters, acetone, ether, and petroleum ether, almost insoluble in water and aqueous bases. It is not stable in mineral acid or strong bases. Analysis of the crystalline acid finds 63.32% C; 9.64% H; 26.90% O.

Some salts of X206 have been found to have the following melting points.

|  |  |
|---|---|
| Sodium | 185°–87°C. |
| Potassium | 211°–13°C. |
| Silver | 153°–56°C. (dec.) |
| Barium | 149.5°–56°C. |

The antibiotic X537A has been disclosed and structurally characterized in Netherlands Patent 70.12,108. The structure is shown below.

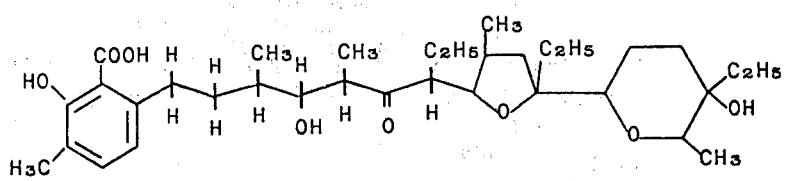

The organism by which X537A is produced by fermentation is on deposit at the International Center of Information on Antibiotics, c/o L. Delcambe, 32, Bd. de la Constitution, Liege, Belgium. The organism is listed on page 41 of the Center's Bulletin No. 3 (1966).

X537A is produced by growing the organism on agar slants for 4 to 6 days. Spores are harvested from the slants and inoculated into shaker flasks containing a medium containing complex nitrogen sources such as soybean meal, cornsteep solids, distillers' residues, or the like. After about 2 to 4 days of growth, the inoculum is used to start cultures in production shaker flasks.

Suitable production media may be based on carbon sources such as starches, sugars, and the like, and on nitrogen sources such as enzyme-digested casein. Maximum production is obtained after about 2 to 3 days' growth at about 25°–30°C. Initial pH of the medium should be about 6.0 to 7.5, and harvest pH should be about 6.5 to 8.0.

Most of the X537A is in the cells. It is isolated by filtering the solids from the fermentation broth and extracting the filter cake with an ester solvent. X537A is precipitated by concentration of the extract, washing with base, further concentration, and addition of petroleum ether. It is purified by recrystallization.

The following example provides a detailed process for making X537A.

EXAMPLE 3

The X537A-producing organism obtained from the I.C.I.A. is inoculated on slants of the following agar.
10 g./l. dextrin
2 g./l. N-Z amine A
1 g./l. beef extract
1 g./l. yeast extract
20 g./l. agar distilled water The cultures are grown for 6 days at 30°C. Then spores are aseptically harvested as a suspension in sterile water.

The spore suspension is used to inoculate starter cultures of the following sterile medium. One ml. of spore suspension is added to each 100 ml. of medium.
15 g./l. cerelose
15 g./l. soybean meal
5 g./l. cornsteep solids
2 g./l. $CaCO_3$
5 g./l. NaCl tap water Starter cultures are grown in 500 ml. shaker flasks on 250-rpm rotary shakers for 36 hours at 30°C.

The harvested starter cultures are used to inoculate production flasks by aseptically adding 5 ml. of starter culture to 100 ml. of the following production medium.
20 g./l. cerelose
10 g./l. soluble starch
30 g./l. peptone
4 g./l. N-Z amine A
5 g./l. $MgSO_4.7H_2O$
5 g./l. blackstrap molasses
2 g./l. $CaCl_2$ tap water Initial pH of the medium is 7.0. The 500-ml. production flasks are shaken for 3 days at 30°C. on a 250-rpm rotary shaker. Final pH at harvest is 7.5.

X537A is isolated from the broth in the following manner. Fifty liters of broth is filtered with diatomaceous filter aid. The wet filter cake is suspended in 25 l. of butyl acetate, and the mixture is stirred overnight at room temperature. The suspension is filtered again, and the water layer of the filtrate is discarded. The butyl acetate layer is concentrated under vacuum to about 750 ml., washed with 10 percent sodium carbonate solution, and dried over anhydrous sodium sulfate. The dried solution is concentrated again to 75 ml. and diluted with an equal volume of petroleum ether. A solid material separates, which is then extracted in a Soxhlet apparatus with 1 l. of petroleum ether for 2 days. The extract is evaporated to dryness, and the residue is suspended in 25 ml. of petroleum ether and filtered, yielding a sodium salt of X537A. The salt is recrystallized from ether-petroleum ether.

The sodium salt is converted to the acid by dissolving in ether and washing with dilute sulfuric acid. Removal of the ether leaves an oily residue which crystallizes from ethanol. The recrystallized acid has a vague melting point of 100°–09°C. The optical rotation of the acid is $[\alpha]_D^{26}$ −7.2° (methanol). The ultraviolet absorption spectrum of the acid shows maxima at 317 m$\mu$ and 249 m$\mu$. Microanalysis finds 67.88 percent carbon and 9.48 percent hydrogen.

The barium salt, m.p. 156°–60°C., the potassium salt, m.p. 177°–78°C., and the sodium salt are conveniently prepared from the free acid by shaking solutions of the free acid in ether with aqueous solutions of the metal hydroxide or carbonate. The salt is in the ether phase in each case. The sodium salt, recrystallized from benzene-ligroin and dried at 100°C., has m.p. of 168°–71°C., and $[\alpha]_D^{26}$ −30° (methanol).

The antibiotics which are operable in my method are all acids, and have the common property of organic acids of forming salts. Representatives of the inorganic bases forming physiologically-acceptable cationic salts with the antibiotics include the alkali metal hydroxides such as lithium hydroxide, sodium hydroxide and potassium hydroxide; the alkali metal carbonates and bicarbonates such as lithium carbonate and sodium bicarbonate; the alkaline earth metal hydroxides and carbonates such as calcium hydroxide and magnesium carbonate; and like inorganic bases.

Illustrative of the organic bases forming physiologically-acceptable salts with the antibiotics are the primary, secondary and tertiary $C_1$–$C_4$ lower alkyl and lower hydroxyalkyl amines such as ethylamine, isopropylamine, diethylamine, methyl-n-butylamine, ethanolamine, and diethanolamine.

The ammonium salts of the antibiotics are prepared with ammonia or ammonium hydroxides.

The salts of the antibiotics are prepared according to procedures commonly employed for the preparation of cationic salts. For example, the free acid form of the antibiotic is dissolved in a suitable solvent, and an aqueous or organic solvent solution of the desired base is added to the antibiotic solution. The antibiotic cationic salts can be isolated by filtration and recrystallization or by evaporation of the solvent and purification by recrystallization.

Physiologically-acceptable esters can readily be made from the acid group of the antibiotics of my method. For example, alkyl esters such as methyl, isopropyl, and butyl, cycloalkyl esters such as cyclopropyl and cyclohexyl, and aryl esters such as phenyl are made by reaction of the acid with a diazo derivative of the substituent to be added. The reaction goes with stirring at room temperature in a suitable solvent such as ether.

Esters can also be made by acylation of one or more of the hydroxy groups of these antibiotics. For example, esters are made by acylation with groups such as formyl, acetyl, hexanoyl and benzoyl by reaction with an anhydride of the group to be added. Reaction occurs in pyridine at room temperature overnight.

The following example shows the method by which the deshydroxymethyl derivatives of monensin and nigericin are made.

EXAMPLE 4

A solution of 10.0 g. of monensin sodium salt and 3.5 g. of sodium borohydride in 250 ml. of absolute ethanol was allowed to stand overnight at room temperature. In the morning, the excess borohydride was decomposed by dropwise addition of acetic acid. The mixture was diluted with 2500 ml. of saturated NaCl solution, and was extracted three times with ether. The combined ether extracts were then washed twice with water and once with saturated NaCl solution. The ether layer was then dried over magnesium sulfate and evaporated to dryness. The residue was 4.0 g. of a mixture of monensin and dihydromonensin, in which the ring opposite the acid group has been opened at the oxygen atom. Dihydromonensin is an amorphous compound. Its NMR spectrum shows a broad singlet at δ3.44.

The residue prepared above was dissolved in 70 ml. of t-butanol and mixed with a solution of 10.3 g. of sodium metaperiodate in 100 ml. of water. The mixture was allowed to stand overnight at room temperature and was evaporated to dryness under vacuum. The residue was taken up in ether and filtered. The filtrate was in turn evaporated to dryness under vacuum to produce 3.68 g. of amorphous product. That product was chromatographed on a 180 g. column of silica gel, first with 1:4 ethyl acetate:benzene and then with 1:3 ethyl acetate:benzene. The eluted fractions which were found to contain deshydroxymethylmonensin were combined, the solvent was evaporated under vacuum, and the product was recrystallized from acetone-water. The product was 1.19 g. of deshydroxymethylmonensin, the melting point of which was 78°–80°C. Its elemental analysis was 65.31 percent C, 9.64 percent H. The structure is shown below.

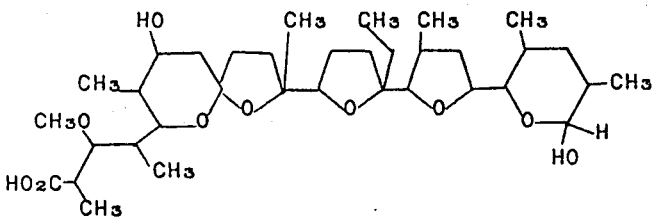

The sodium salt of deshydroxymethylmonensin, m.p. 155°–158°C., was made by titrating a sample of the acid form with NaOH solution, and extracting the reaction mixture with ether. An IR spectrum of the sodium salt exhibits a strong band at 6.42 and a weak band at 5.91μ. Its NMR spectrum shows a singlet at δ3.37, and a doublet at δ5.26.

It is well known in the veterinary pharmaceutical art that conditions within the animal frequently change an antibiotic to chemical forms other than that in which it was administered. Therefore, the form in which it may be administered does not affect the method of treatment and may be chosen for reasons of economics, convenience, and toxicity.

The experimental examples which follow show that the antibiotic molecules which have been modified by formation of physiologically-acceptable esters and salts are effective in my method. The terms X206, A204, nigericin, X537A, monensin, and dianemycin are used in this specification and claims to include physiologically-acceptable esters and salts of those antibiotics.

The effectiveness of my method of modifying the ratio of volatile fatty acids produced in the rumen was first proven by means of in vitro tests. The test method I used is shown below.

EXAMPLE 5

Rumen fluid is obtained from a steer which has a surgically-installed fistula opening into the rumen. The steer is maintained on a high-grain ration, the composition of which follows:

| | |
|---|---|
| 69.95% | coarse ground corn |
| 10% | ground corncobs |
| 8% | soybean meal (50% protein) |
| 5% | alfalfa meal |
| 5% | molasses |
| 0.6 | urea |
| 0.5% | dicalcium phosphate |
| 0.5% | calcium carbonate |
| 0.3% | salt |
| 0.07% | Vitamin A and $D_2$ premix |
| 0.05% | Vitamin E premix |
| 0.03% | trace mineral premix |

A sample of rumen fluid is strained through four layers of cheesecloth and the eluate is collected in a vacuum bottle. The particulate matter retained by the cheesecloth is resuspended in enough physiological buffer to return it to the original volume of the rumen fluid, and the eluate is strained again. The buffer used is described below:

0.316 g./l. $Na_2HPO_4$
0.152 g./l. $KH_2PO_4$
2.260 g./l. $NaHCO_3$
0.375 g./l. KCl
0.375 g./l. NaCl
0.112 g./l. $MgSO_4$
0.038 g./l. $CaCl_2$
0.008 g./l. $FeSO_4 \cdot 7H_2O$
0.004 g./l. $MnSO_4$
0.004 g./l. $ZnSO_4 \cdot 7H_2O$
0.002 g./l. $CuSO_4 \cdot 5H_2O$
0.001 g./l. $CoCl_2$ Cheng et al., *J. Dairy Sci.* 38, 1225, (1955).

The two eluates are pooled in a separatory funnel and allowed to stand till particulate matter separates to the top. The clear layer is then diluted 1:1 with the same buffer, and adjusted to pH 7.0 with HCl or NaOH.

Ten ml. of the diluted rumen fluid prepared above is placed in a 25 ml. flask with 40 mg. of the same feed shown above. The compound to be tested is weighed out and dissolved in an appropriate solvent. The solution is placed on the finely powdered ration in each test flask and dried. Five mg. of soybean protein is also added per flask. Four replicate flasks are used per treatment.

Two sets of four untreated control flasks each are also prepared. One set of control flasks is incubated for 16 hours at 38°C. with the test flasks. The other set of four untreated control flasks are zero-time controls, to which 2 ml. of 25 percent metaphosphoric acid is added as soon as the flasks are prepared to stop the fermentation.

Fermentation in the incubated test and control flasks is stopped at the end of 16 hours by addition of 2 ml. of 25 percent metaphosphoric acid to each flask.

All of the samples are allowed to settle, and the supernatant is analyzed by gas chromatographic methods for acetate, propionate, and butyrate.

The analysis for each volatile fatty acid found in the zero-time controls is subtracted from the analyses of the untreated controls and of the test flasks. The resulting values reflect the amount of each VFA produced during the 16-hour fermentation period. The values obtained from the four replicate flasks on each treatment are averaged.

The data below are reported as the ratio of VFA's produced in treated flasks to VFA's produced in untreated control flasks. This method of reporting the data shows most clearly the results of the changes in the chemistry of the rumen brought about by my method of feed utilization improvement.

| Compound | Rate | | Acetate | Propionate | Butyrate |
|---|---|---|---|---|---|
| Monensin Na Salt | 100 | mcg./ml. | 1.08 | 0.96 | 0.84 |
| | 50 | | 0.89 | 1.90 | 0.56 |
| | 25 | | 0.94 | 1.91 | 0.49 |
| | 10 | | 0.94 | 1.56 | 0.80 |
| | 5 | | 0.81 | 1.91 | 0.70 |
| | 2 | | 0.91 | 1.76 | 0.95 |
| | 1 | | 0.89 | 1.41 | 0.80 |
| | 0.5 | | 0.95 | 1.25 | 0.82 |
| | 0.25 | | 0.97 | 1.15 | 0.87 |
| Monensin diacetate | 50 | mcg./ml. | 1.05 | 1.27 | 0.65 |
| | 25 | | 1.05 | 1.04 | 0.86 |
| | 10 | | 0.97 | 1.26 | 0.82 |
| | 5 | | 1.11 | 0.97 | 0.86 |
| | 1 | | 1.09 | 0.93 | 0.92 |
| Deshydroxymethyl-monensin | 25 | | 0.89 | 2.00 | 0.39 |
| | 10 | | 0.89 | 1.55 | 0.84 |
| | 5 | | 0.90 | 1.68 | 0.52 |
| | 1 | | 0.94 | 1.42 | 0.82 |
| | 0.2 | | 0.93 | 1.15 | 0.93 |
| | 0.25 | | 0.95 | 1.24 | 0.93 |
| Acetyl monensin | 0.25 | | 0.92 | 1.37 | 0.86 |
| A204 I | 25 | | 1.06 | 1.83 | 0.39 |
| | 1 | | 0.94 | 1.18 | 0.90 |
| | 0.25 | | 0.98 | 1.09 | 0.89 |
| A204 II | 25 | | 1.00 | 1.49 | 0.67 |
| | 10 | | 0.90 | 1.55 | 0.86 |
| | 1 | | 0.94 | 1.34 | 0.77 |
| | 0.5 | | 0.92 | 1.31 | 0.78 |
| | 0.25 | | 0.93 | 1.28 | 0.81 |
| X206 | 10 | | 0.93 | 1.32 | 0.70 |
| | 2 | | 0.97 | 1.17 | 0.89 |
| | 0.5 | | 1.01 | 1.08 | 0.89 |
| Dianemycin | 25 | mcg./ml. | 1.00 | 1.74 | 0.63 |
| | 10 | | 0.92 | 1.56 | 0.79 |
| | 5 | | 1.03 | 1.60 | 0.66 |
| | 1 | | 0.99 | 1.21 | 0.87 |
| | 0.5 | | 1.00 | 1.10 | 0.89 |
| | 0.2 | | 1.03 | 1.13 | 0.87 |
| | 0.25 | | 0.99 | 1.07 | 0.94 |
| | 0.1 | | 1.02 | 0.99 | 0.97 |
| Nigericin | 25 | | 0.89 | 1.56 | 0.76 |
| | 10 | | 0.84 | 1.48 | 0.88 |
| | 5 | | 0.86 | 1.72 | 0.70 |
| | 1 | | 0.92 | 1.26 | 0.88 |
| | 0.5 | | 0.93 | 1.18 | 0.92 |
| | 0.2 | | 0.97 | 1.14 | 0.88 |
| | 0.25 | | 0.90 | 1.16 | 0.98 |
| Deshydroxymethyl-nigericin | 0.25 | | 0.97 | 1.13 | 0.97 |
| Acetyl nigericin | 10 | | 0.88 | 1.39 | 0.75 |

-continued

| Compound | Rate | Acetate | Propionate | Butyrate |
|---|---|---|---|---|
|  | 2 | 1.01 | 1.30 | 0.72 |
|  | 0.5 | 1.03 | 1.18 | 0.76 |
|  | 0.25 | 0.97 | 1.10 | 0.97 |
| X537A | 10 | 0.83 | 1.80 | 0.73 |
|  | 5 | 0.82 | 2.03 | 0.71 |
|  | 1 | 0.96 | 1.23 | 0.88 |
|  | 0.2 | 1.02 | 1.06 | 0.95 |

EXAMPLE 6

The following tests were done in exactly the same way except that the rumen fluid which was put into the system was obtained from slaughtered sheep, rather than fistulated cattle.

| Compound | Rate | Acetate | Propionate | Butyrate |
|---|---|---|---|---|
| Monensin Na Salt | 50 mcg./ml. | 0.97 | 1.77 | 0.39 |
| Monensin Na Salt | 10 mcg./ml. | 0.94 | 1.79 | 0.45 |

EXAMPLE 7

In order to prove that my method is not limited to ruminants fed on high-protein or high-energy diets, the following in vitro experiment was performed. The procedure was exactly as Example 5 except that the rumen fluid was obtained from a steer on an all-roughage diet, and the substrate supplied to the flasks was ground alfalfa hay. The test compound was monensin sodium salt.

| Rate | Acetate | Propionate | Butyrate |
|---|---|---|---|
| 25 mcg./ml. | 0.87 | 1.34 | 0.85 |
| 5 mcg./ml. | 0.86 | 1.34 | 0.84 |
| 1 mcg./ml. | 0.96 | 1.11 | 1.06 |
| 0.2 mcg./ml. | 0.99 | 1.05 | 1.13 |
| 0.04 mcg./ml. | 1.00 | 1.00 | 1.03 |

The data above show that my method is effective in increasing production of propionates in the rumen of animals on a low-energy diet.

The data tabulated above show that all the antibiotics named are effective in increasing propionate production in the rumen, regardless of the form in which the antibiotic is fed and regardless of the diet which the ruminants may be fed.

Further tests have been conducted in vivo. The tests were performed in animals which have had fistulas installed in their rumens. It is thus possible to withdraw specimens of the contents of the rumen.

The animal is fed a known amount of a known diet each day containing an accurately measured dose of the compound. If the animal should choose not to eat his whole daily ration, the uneaten portion is placed directly in the rumen through the fistula. Two hours after feeding, a sample of the rumen fluid is taken from the animal and several 100 ml. aliquots are placed in flasks. Fermentation is topped immediately in some of the flasks by addition of 50 ml. of 25 percent metaphosphoric acid. The other flasks are incubated at 38°C. After one hour, fermentation in the incubated flasks is stopped in the same way.

Thus, the production of VFA's in the rumen fluid is measured over a 1-hour period, without the interference of absorption from the rumen which is actually occurring in the animal at all times.

The contents of each flask are strained through four layers of cheesecloth and centrifuged at 1500 rpm for 10 minutes. The eluate is analyzed for VFA contents by a gas chromatograph. The production of acetate, propionate, and butyrate over the 1-hour period is determined by subtracting the zero-time concentrations from the concentrations measured in the incubated samples.

EXAMPLE 8

The test reported in the following table was conducted with mature fistulated steers weighing about 1,000 kg. each. Two steers were fed a normal diet, similar to the high-grain feed shown above, and two steers in each treatment group were fed the identical diet but with monensin sodium salt added. The results are shown below as the changes in the concentrations in the rumen of acetate, propionate, and butyrate measured in millimoles per liter of rumen fluid. The number reported is the concentration of the treated samples, averaged over four analyses in a 14-day treatment period, minus the average concentration during a control period before treatment.

| Level | Acetate | Propionate | Butyrate |
|---|---|---|---|
| Control | −5.7 | −1.3 | −1.5 |
| Control | 6.0 | 5.4 | 2.8 |
| .2 mg./kg./day | −3.2 | 10.9 | −3.1 |
| .5 mg./kg./day | −0.8 | 30.1 | −7.0 |
| .5 mg./kg./day | 4.4 | 17.2 | −3.3 |

The data from the cattle test above can also be shown as changes in propionate production. The table below shows the ratio of propionate production of the cattle during the treatment period of the propionate production of the same cattle during a control period before treatment.

| Monensin Level | Ratio of Production |
|---|---|
| Control | 1.06 |
| Control | 1.05 |
| 0.2 mg./kg./day | 1.60 |
| 0.5 mg./kg./day | 2.43 |
| 0.5 mg./kg./day | 2.12 |

It is clear that propionate production is sharply increased over control animals when monensin is added to the cattle's diet.

EXAMPLE 9

Similar tests were performed with fistulated sheep. The results of those tests, expressed as changes in concentrations, are shown in this table.

| Level | Acetate | Propionate | Butyrate |
|---|---|---|---|
| Control | 20.6 | 2.7 | 3.7 |
| 0.8 mg./kg./day | 14.4 | 14.8 | −0.3 |
| 1.0 mg./kg./day | 9.8 | 14.9 | −1.3 |

It will be seen that the monensin treatments reduced acetate concentration as compared with the controls. It is obvious that the propionate concentration was increased by treatment with monensin.

The tests which have been reported above also showed subjective evidence of reduced susceptibility to bloat of the treated animals. Bloat is a highly harmful condition which results from excess gas accumulation in the rumen. The afflicted animal is unable to dispose of the gas by eructation due to the entrapment of gas in a stable foam. Foaminess of the rumen is a predisposing factor for bloat.

The animals treated in the tests shown above had rumen contents before treatment with monensin which were consistently quite foamy. The operators performing the tests noticed foaminess in the control animals and in the treated animals before treatment was begun. However, as soon as treatment with the antibiotic compound was begun, the foaminess in treated cattle decreased. The change in foaminess of rumen contents was observed in 5 of the 6 treated cattle. Thus, it is believed that an additional benefit of oral administration of the antibiotic compounds of my method is a decreased susceptibility to bloat.

EXAMPLE 10

Six fistulated Hereford heifers weighing an average 325 kg. were randomly allotted to 3 groups. All groups were given monensin sodium salt in their diet at the rates shown in the table.

On the 9th and 16th days of monensin administration, samples of rumen contents were taken from each animal and analyzed for VFA. The data are reported as ratios of molar concentrations, in the order acetate/propionate/butyrate.

The data show very clearly the beneficial effects of my method of increasing feed utilization by increasing propionate concentration in the rumen.

The published control ratio is 2.90/1/0.64. Hungate, *The Rumen and Its Microbes*, page 270, Academic Press.

| | Monensin Rate | | |
|---|---|---|---|
| | 1.3 mg./kg./day | 1.7 mg./kg./day | 2.0 mg./kg./day |
| Ratio, Day 9 | 0.84/1/0.10 | 0.81/1/0.10 | 0.91/1/0.15 |
| Ratio, Day 16 | 1.09/1/0.11 | 1/1/0.11 | 1.03/1/0.12 |

In this experiment, the data show that the animals' feed utilization has been changed dramatically. As compared with the control, the ratio of propionate to acetate has been tripled, and the ratio of propionate to butyrate has been increased by a factor of more than five.

Administration of the antibiotic compounds of my method prevents and treats ketosis as well as improves feed utilization. The causative mechanism of ketosis is a deficient production of propionate compounds. A presently recommended treatment is administration of propionic acid or feeds which preferentially produce propionates. It is obvious that my method, which encourages propionate production from ordinary feeds, will reduce incidence of ketosis.

I have found that monensin and the other antibiotic compounds of my method increase the efficiency of feed utilization in ruminant animals when they are administered orally to the animals. The easiest way to administer the antibiotics is by mixing them in the animal's feed.

However, the antibiotic compounds can be usefully administered in other ways. For example, they can be incorporated into tablets, drenches, boluses, or capsules, and dosed to the animals. Formulation of the antibiotic compounds in such dosage forms can be accomplished by means of methods well known in the veterinary pharmaceutical art.

Capsules are readily produced by filling gelatin capsules with any desired form of the desired antiobiotic. If desired, the antiobiotic can be diluted with an inert powdered diluent, such as a sugar, starch, or purified crystalline cellulose in order to increase its volume for convenience in filling capsules.

Tablets of the antibiotics of my method are made by conventional pharmaceutical processes. Manufacture of tablets is a well-known and highly advanced art. In addition to the active ingredient, a tablet usually contains a base, a disintegrator, an absorbent, a binder, and a lubricant. Typical bases include lactose, fine icing sugar, sodium chloride, starch and mannitol. Starch is also a good disintegrator as is alginic acid. Surface-active agents such as sodium lauryl sulfate and dioctyl sodium sulphosuccinate are also sometimes used. Commonly-used absorbents again include starch and lactose while magnesium carbonate is also useful for oily substances. Frequently-used binders are gelatin, gums, starch, dextrin and various cellulose derivatives. Among the commonly used lubricants are magnesium stearate, talc, paraffin wax, various metallic soaps, and polyethylene glycol.

My method can also be practiced by the administration of the antibiotic compound as a slow-pay-out bolus. Such boluses are made as tablets are made except that a means to delay the dissolution of the antibiotic is provided. Boluses are made to release for lengthy periods. The slow dissolution is assisted by choosing a highly water-insoluble form of the antibiotic. A substance such as iron filings is added to raise the density of the bolus and keep it static on the bottom of the rumen.

Dissolution of the antibiotic is delayed by use of a matrix of insoluble materials in which the drug is embedded. For example, substances such as vegetable waxes, purified mineral waxes, and water-insoluble polymeric materials are useful.

Drenches of my antibiotics are prepared most easily by choosing a water-soluble form of the antibiotic. If an insoluble form is desired for some reason, a suspension may be made. Alternatively, a drench may be formulated as a solution in a physiologically-acceptable solvent such as a polyethylene glycol.

Suspensions of insoluble forms of my antibiotics can be prepared in nonsolvents such as vegetable oils such as peanut, corn, or sesame oil; in a glycol such as propylene glycol or a polyethylene glycol; or in water, depending on the form of the antibiotic chosen.

Suitable physiologically-acceptable adjuvants are necessary in order to keep the antibiotic suspended. The adjuvants can be chosen from among the thickeners, such as carboxymethylcellulose, polyvinylpyrrolidone, gelatin, and the alginates. Many classes of surfactants serve to suspend antibiotics. For example, lecithin, alkylphenol polyethylene oxide adducts, naphthalenesulfonates, alkylbenzenesulfonates, and the polyoxyethylene sorbitan esters are useful for making suspensions in liquid nonsolvents.

In addition many substances which effect the hydrophilicity, density, and surface tension of the liquid can assist in making suspensions in individual cases. For example, silicone anti-foams, glycols, sorbitol, and sugars can be useful suspending agents.

The suspendable antibiotic may be offered to the grower as a suspension, or as a dry mixture of the antibiotic and adjuvants to be diluted before use.

My antibiotics may also be administered in the drinking water of the ruminants. Incorporation into drinking water is performed by adding a water-soluble or water-suspendable form of the desired antibiotic to the water in the proper amount. Formulation of the antibiotic for addition to drinking water follows the same principles as formulation of drenches.

The most practical way to treat animals with the antibiotic compounds of my method is by the formulation of the compound into the feed supply. Any type of feed may be medicated with the antibiotic compounds, including common dry feeds, liquid feeds, and pelleted feeds.

The methods of formulating drugs into animal feeds are well known. It is usual to make a concentrated drug premix as a raw material for medicated feeds. For example, typical drug premixes may contain from about one to about 400 grams of drug per pound of premix. The wide range results from the wide range of concentration of drug which may be desired in the final feed. Premixes may be either liquid or solid.

The formulation of ruminant feeds containing the proper amounts of my antibiotic compounds for useful treatment is well understood. It is necessary only to calculate the amount of compound which it is desired to administer to each animal, to take into account the amount of feed per day which the animal eats and the concentration of antibiotic compound in the premix to be used, and calculate the proper concentration of antibiotic compound, or of premix, in the feed.

All of the methods of formulating, mixing, and pelleting feeds which are normally used in the ruminant feed art are entirely appropriate for manufacturing feeds containing the antibiotic compounds of my method.

It is not my intention to limit the scope of my invention to any particular formulations or methods of administration. My invention is a method of increasing the efficiency of feed utilization by ruminant animals by the oral administration of certain antibiotics. However the administration may be accomplished, it remains my method.

It is usual to treat economic animals, including ruminants, with a variety of growth promotors, diseasepreventives, and disease treatments throughout their lives. Such drugs are often used in combination. My method may be practiced in combination with other treatments.

As has been shown, oral administration of the antibiotics effective in my method beneficially alters the production of propionates relative to the production of acetates in the rumen. The same treatment also benefits monogastric animals which ferment fibrous vegetable matter in the cecum. The monogastric animals here referred to are those which consume fibrous vegetable food and digest at least part of it by microbiological fermentation in the cecum. The cecal fermentation follows a chemical pathway similar to rumen fermentation.

Horses, swine, and rabbits are exemplary animals which digest a part of their food by cecal fermentation. The overall feed utilization of such animals is improved by the oral administration of the antibiotics effective in my method by means of a beneficial change in the propionate/acetate ratio. Horses and rabbits are exemplary of animals in which cecal fermentation is a major part of the total digestive process, and in which my antibiotics are accordingly particularly beneficial.

I claim:

1. A method of increasing the efficiency of feed utilization by ruminant animals having a developed rumen function which comprises the oral administration to such animals of a propionate-increasing amount of an antibiotic selected from the group consisting of X206, dianemycin, nigericin, the deshydroxymethyl derivative of nigericin, and their physiologically acceptable esters and salts.

2. The method of claim 1 wherein the ruminant animals are cattle.

3. The method of claim 1 in which the ruminant animals are sheep.

4. The method of claim 1 in which the compound is administered at a rate of from about 0.05 mg./kg./day to about 2.5 mg./kg./day.

5. The method of claim 1 in which the compound is administered at a rate of from about 0.1 mg./kg./day to about 1.5 mg./kg./day.

6. The method of claim 5 in which the ruminant animals are cattle.

7. The method of claim 5 in which the ruminant animals are sheep.

8. The method of claim 1 in which the compound administered is selected from the group consisting of X206 and its physiologically-acceptable esters and salts.

9. The method of claim 1 in which the compound administered is selected from the group consisting of dianemycin and its physiologically-acceptable esters and salts.

10. The method of claim 1 in which the compound administered is selected from the group consisting of nigericin, the deshydroxymethyl derivative of nigericin, and their physiologically-acceptable esters and salts.

* * * * *

UNITED STATES PATENT AND TRADEMARK OFFICE
CERTIFICATE OF CORRECTION

PATENT NO. : 3,937,836
DATED : February 10, 1976
INVENTOR(S) : Arthur P. Raun

It is certified that error appears in the above-identified patent and that said Letters Patent are hereby corrected as shown below:

In the Abstract, line 3, "monesin" should read --monensin--.

Column 2, line 65, "monoensin" should read --monensin--.

Column 9, line 60, "20 g./l. agar distilled water" should read --20 g./l. agar--.

Column 9, insert between lines 60 and 61, the words --distilled water--.

Column 10, line 3, "5 g./l. NaCl tap water" should read --5 g./l. NaCl--.

Column 10, insert between lines 3 and 4, the words --tap water--.

Column 10, line 15, "2 g./l. $CaCl_2$ tap water" should read --2 g./l. $CaCl_2$--.

Column 10, insert between lines 15 and 16, the words --tap water--

Signed and Sealed this eighteenth Day of May 1976

[SEAL]

Attest:

RUTH C. MASON
*Attesting Officer*

C. MARSHALL DANN
*Commissioner of Patents and Trademarks*